United States Patent [19]

Lutkowski

[11] 4,416,290
[45] Nov. 22, 1983

[54] MULTIPLE SAMPLE NEEDLE ASSEMBLY WITH VEIN INDICATION

[75] Inventor: Lawrence Lutkowski, East Rutherford, N.J.

[73] Assignee: Becton Dickinson and Company, Paramus, N.J.

[21] Appl. No.: 412,647

[22] Filed: Aug. 30, 1982

[51] Int. Cl.³ .............................................. A61B 5/14
[52] U.S. Cl. ................................... 128/764; 128/771
[58] Field of Search ............. 128/763, 764, 765, 766, 128/770, 771, 214.4

[56] References Cited

U.S. PATENT DOCUMENTS

| | | | |
|---|---|---|---|
| 3,640,393 | 2/1972 | Hurtig | 128/771 X |
| 3,734,080 | 5/1973 | Petterson et al. | 128/764 |
| 3,814,079 | 6/1974 | Le Roy | 128/764 |
| 3,877,465 | 4/1975 | Miyake | 128/764 |
| 4,066,067 | 1/1978 | Micheli | 128/764 |
| 4,207,870 | 6/1980 | Eldridge | 128/766 |
| 4,312,362 | 1/1982 | Kaufman | 128/763 |
| 4,340,068 | 7/1982 | Kaufman | 128/766 |

*Primary Examiner*—Edward M. Coven

[57] ABSTRACT

A multiple liquid sample needle assembly is provided which utilizes a housing with a porous filter which is gas permeable and liquid impermeable for providing gas displacement venting for gas displaced by a liquid sample received in the housing. The invention incorporates a translucent or transparent housing for determining whether access to the liquid sample in question has been obtained. The filter of the assembly cooperates with the sequential application of a plurality of vacuum collection tubes to close off passage of air therethrough during the taking of the samples. In addition, the assembly is arranged to accommodate separate I.V. and negative pressure cannulas, or a single cannula with an I.V. and negative pressure point at opposite ends thereof.

8 Claims, 3 Drawing Figures

MULTIPLE SAMPLE NEEDLE ASSEMBLY WITH VEIN INDICATION

BACKGROUND AND STATEMENT OF THE INVENTION

This invention relates to an assembly for collecting a liquid sample from a patient, such as a blood sample. More particularly, this invention relates to a needle assembly for collecting sequentially multiple liquid samples from such a patient. The device of the invention utilizes a receiving chamber with walls which are translucent or transparent for visually indicating whether or not proper access to the source of the sample in question has been achieved. Moreover, the housing or chamber which receives the sample incorporates therein a porous filter which filter is comprised of a material which provides, simultaneously, a liquid barrier for the sample received in the housing, and a gas displacement discharge passage for gas displaced by the liquid sample received in the chamber.

The filter in the housing is positioned in such a way that it extends from the chamber to an exit point for the discharge of gas out of the housing chamber, which exit point may be covered by the cooperative engagement of the flange of the rubber sleeve or valve means which extends over the discharge opening of the negative pressure cannula during periods when a sample is not being discharged therefrom into an evacuated tube. Subsequently, when a liquid sample is to be discharged into an evacuated tube placed over the negative pressure cannula, the stopper for the tube engages the sleeve in a conventional manner. The negative pressure point of the negative pressure cannula passes through the stopper of the evacuated tube and the stopper moves along the negative pressure cannula toward the housing. In doing so, the point of the negative pressure cannula pierces the sleeve, and causes the sleeve to collapse and move toward the adjacent housing face. Thus, the flange of the sleeve is caused to engage the housing face, closing off the exit end of the filter device. For this reason, when a sample is being collected from the housing chamber into an evacuated tube, no air is allowed to pass through the filter from outside into the chamber.

Once the evacuated tube is withdrawn from the negative pressure cannula, the sleeve moves outwardly to reseal the discharge opening of the negative pressure cannula and the sample chamber in the assembly housing until the next evacuated tube is inserted into the assembly. Thus, with the sequential application of a series of evacuated tubes, the tubes move the sleeve out of engagement with the negative pressure discharge opening or point of the negative pressure cannula, and cause the flange of the sleeve to engage the exit opening of the filter to prevent any air passing into the sample chamber.

As discussed above, it is desirable to provide a mechanism whereby the user of such a needle assembly can be informed when the intravenous needle has penetrated the vein of the patient for collecting a blood sample. Many times, in collecting blood from a patient, it is difficult to locate the vein, or for other reasons blood flow into the collecting device is not adequate. In those instances, it is advantageous to be able to make a quick determination that entry into the vein has been made and that blood is flowing into the needle assembly.

Once this determination has been made and the vein entry achieved, the evacuated blood collection containers can be inserted, sequentially, as discussed above, into the collection assembly in accordance with well known techniques of collecting blood samples during a single collection procedure. Thus, by utilizing a translucent or transparent chamber, with the assembly of the invention herein, the fact that blood flow has been obtained is quickly realized simply by the user visually noting blood collecting in the housing chamber of the assembly of the invention here. Furthermore, as discussed above, with the utilization of the porous filter in the housing wall, the filter allows for displacement of the air from the housing chamber so as to allow room for receiving the blood sample being collected.

A prior art device which recognizes the utilization of a porous material for providing a venting for displaced air during receiving a blood sample is taught in U.S. Pat. No. 4,207,870, issued June 17, 1980. That assembly requires a separate one-way valve construction which opens and allows blood to travel from the vein of the patient and through the housing and into an evacuated container. Other related applications include co-pending U.S. applications Ser. No. 160,781 filed June 18, 1980, now U.S. Pat. No. 4,340,068, issued July 20, 1982, Ser. No. 284,894 filed July 20, 1981 and Ser. No. 311,494 filed Oct. 15, 1981.

Other objects and advantages of this invention will be apparent from the following description, the accompanying drawings and the appended claims.

DETAILED DESCRIPTION OF THE DRAWINGS

Figure 1:
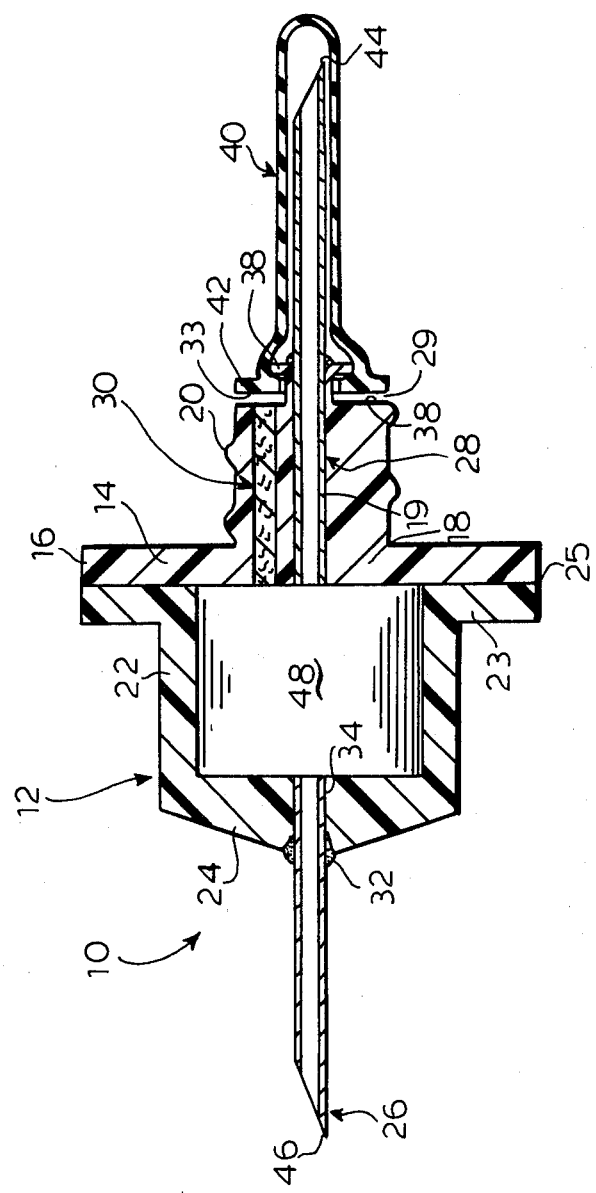
Figure 2:
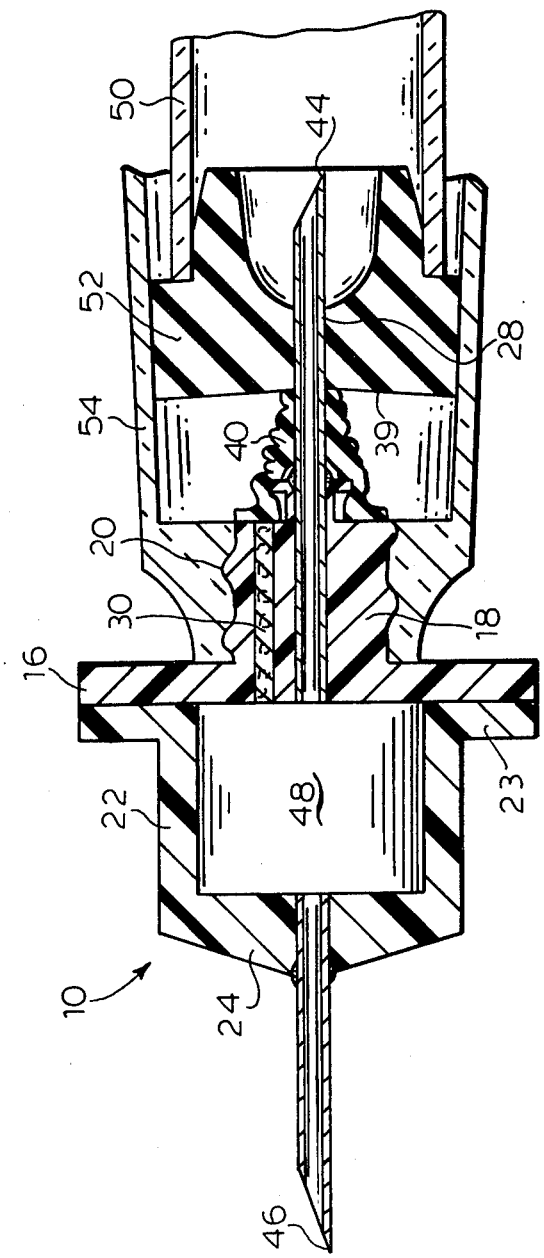
Figure 3:
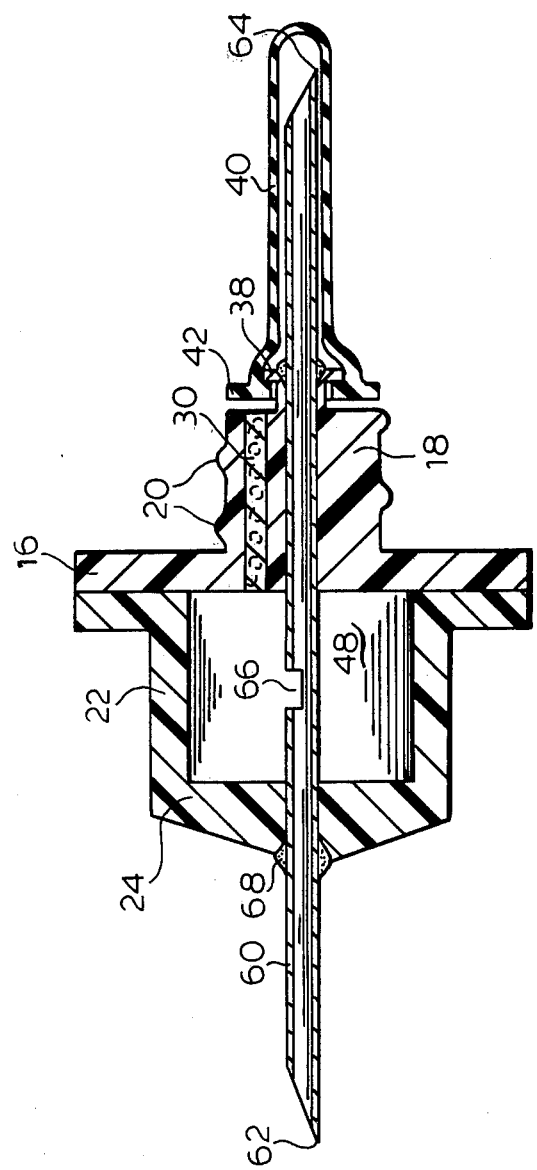

FIG. 1 is a longitudinal sectional view illustrating one embodiment of the invention;

FIG. 2 is a longitudinal sectional view of the assembly of FIG. 1 having applied thereto an evacuated tube holder together with an evacuated tube indicating the valve closing structure of the invention; and FIG. 3 is a longitudinal sectional view of an assembly similar to that of FIG. 1, but illustrating a further embodiment of the invention with a single cannula with a negative pressure and intravenous point at opposite ends thereof.

DETAILED DESCRIPTION OF THE INVENTION

Referring to the drawings, in which like reference characters refer to like parts throughout the several views thereof, FIG. 1 shows the basic components of needle assembly 10 including a hub assembly 12 with an annular housing 22 which is translucent or transparent for indicating the presence of blood in chamber 48 defined by annular housing 22. The hub assembly includes a front wall 24 with a bore 34 therethrough for receiving an intravenous cannula 26 having a point 46, which cannula 26 is fixed in bore 34 by appropriate adhesive 32. The assembly includes a rear housing portion 14 having a front flange 16 for cooperating with a rear flange 23 of hub assembly 12. The flanges 16, 23 are bonded at 25 with a conventional adhesive. Rear housing portion 14 includes an annular rear extension 18 with helical turns 20 on the outer surface thereof for receiving an evacuated tube holder thereon, as will be discussed below. Rear extension 18 includes, further, a bore 19 for receiving a negative pressure cannula 28 therein.

As can be seen in FIG. 1, negative pressure cannula 28 includes a point 44 at the discharge end thereof. Negative pressure cannula 28 is fixed in bore 19 by an appropriate adhesive 36. Extending from the rear face 31 of rear extension 18 is a rear flange 38 for receiving thereover the rubber sleeve 40. The flange 38 cooperates with flange 42 of sleeve 40 to hold sleeve 40 in place over negative pressure cannula 28, as shown in FIG. 1. The front face 33 of sleeve flange 42, as can be seen in FIG. 1 is spaced from rear face 31 of extension 38 to define an air passage 29. As can be seen in FIG. 1, further, a sintered filter 30 extends through rear extension 18 from chamber 48 to rear face 31. Filter 30 is comprised of a material which is gas permeable, and liquid impermeable. As purely illustrative of materials which may be used to form filter 30, sintered polyethylene may be selected or an open cell polyethylene foam or other similar moldable polymeric materials such as porous polypropylene, or porous polyfluorocarbons.

Referring now to FIG. 2, assembly 10 is shown with an evacuated tube holder 54 received on the helical turns 20 of rear extension 18. Received in holder 54 in conventional manner is an evacuated tube 50, the stopper 52 of which has been penetrated by the point 44 of negative pressure cannula 28, in the usual manner. As can be seen, further, in FIG. 2, front face 39 of stopper 52 has engaged and caused the collapse of rubber sleeve 40. This engagement has urged flange 42 of sleeve 40 against the rear face 31 of rear extension 18 closing passage 29, and front face 33 of flange 42 covers the exit end of filter 30. As will be appreciated, at this point in the use of the device of the invention, intravenous point 46 of I.V. cannula 26 will have penetrated the vein of a patient so that blood has passed through I.V. cannula 26 into chamber 48. Any air in the chamber will have passed through filter 30, and passage 29. The user will observe that such penetration has taken place because blood will be indicated in the translucent or transparent chamber 48 defined by the annular housing 22. Thus, upon penetration of point 44 through stopper 52 of the evacuated tube 50, the negative pressure will cause the blood collected in chamber 48 to pass through negative pressure cannula 28 into evacuated chamber 50. Because the filter 30 is closed at the outer end thereof, no air may return to chamber 48.

As will be appreciated, once a sample has been obtained from chamber 48, and is contained in evacuated tube 50, it may be removed from negative pressure cannula 28. This removal causes the rubber sleeve 40 to move back to the position shown in FIG. 1 for resealing of negative pressure cannula 28, until the sequential insertion of the next evacuated tube 50. It will be appreciated, further, that I.V. cannula point 46 will remain in the vein of a patient during this exchange of evacuated tubes 50.

Referring now to FIG. 3, a further embodiment of the invention is shown in which a single cannula 60 is utilized having a negative pressure point 64 and intravenous point 62. In order to provide communication between the cannula 60 and chamber 48 defined by the transparent annular housing 22, a slot 66 is formed in cannula 60. Cannula 60 is fixed in bore 34 of the front wall 24 of the intravenous hub assembly 12 by an appropriate adhesive 68 as will be appreciated. The remaining parts of the assembly of FIG. 3 are the same as those shown and described in FIG. 1.

Thus, as will be appreciated from the above discussion, a blood collection needle assembly is provided in accordance with this invention for collecting multiple samples, as required, in combination with an arrangement for indicating vein entry to the user of the assembly. Moreover, the arrangement of the invention here is in the form of a simplified porous filter operating to provide, simultaneously, passage of a gas and blockage of a liquid. A conventional sleeve for blocking the discharge end of the negative pressure cannula is utilized in combination to provide a closing off or valving of the filter preventing air passage during periods of taking of samples, with the sleeve being moved into engagement for blocking or valving the filter by the sequential insertion of the negative pressure cannula into a plurality of evacuated tubes for receiving the separate multiple blood samples. The arrangement of apparatus herein, as will be appreciated, is an extremely simplified and an inexpensive arrangement of apparatus for manufacturing. It is particularly appropriate for mass production techniques, since the device of the invention will be used only once and then thrown away, after multiple samples have been taken with a single vein entry.

While the methods and forms of apparatus herein described constitute preferred embodiments of this invention, it is to be understood that the invention is not limited to those precise methods and forms of apparatus and that changes may be made therein without departing from the scope of the invention which is defined in the appended claims.

What is claimed is:

1. A needle assembly for collecting one or more liquid samples from a source for subsequent discharge sequentially into a plurality of evacuated containers, comprising
   (a) a housing defining a sample collection chamber therein;
   (b) a front wall on said housing;
   (c) a rear wall on said housing;
   (d) an intravenous point spaced from said front wall;
   (e) a negative pressure point spaced from said rear wall;
   (f) cannula means extending from said intravenous point to said negative pressure point;
   (g) means in said cannula means for communicating the lumen of said cannula means with said sample collection chamber;
   (h) a resilient sleeve extending over the portion of said cannula means extending from said back wall to said negative pressure point;
   (i) a flange on said sleeve on the end thereof adjacent said rear wall;
   (j) a passage containing a gas permeable, liquid impermeable filter extending from said chamber through said rear wall; and
   (k) a flat surface on said sleeve flange for cooperating with said rear wall for blocking gas from passing through said filter;
   (l) whereby when said intravenous point engages said source, liquid enters said chamber through said communicating means by forcing gas in said chamber through said filter, and when said negative pressure point comes in contact with an evacuated container the stopper thereof causes collapse of said sleeve, moving said sleeve flange against said rear wall for cooperating blockage of said passage.

2. The apparatus of claim 1, further characterized by
   (a) said filter is comprised of a member selected from the group consisting of sintered polyethylene, open cell polyethylene foam, porous polypropylene, porous polyfluorocarbons, and mixtures thereof.
3. The apparatus of claim 1, further characterized by
(a) said cannula means comprises
  (1) an intravenous cannula extending between said intravenous point and said front wall, the lumen of said intravenous cannula in flow communication with said chamber; and
  (2) a negative pressure cannula extending between said negative pressure point and said rear wall, the lumen of said negative pressure cannula in flow communication with said chamber.
4. The apparatus of claim 1, further characterized by
(a) said housing including means for connecting a holder for an evacuated container.
5. The apparatus of claim 4, further characterized by
(a) a holder for an evacuated container connected to said housing.
6. The apparatus of claim 1, further characterized by
(a) said housing including means for viewing the contents of said sample collection chamber.
7. The apparatus of claim 6, further characterized by
(a) said viewing means is a translucent housing defining said chamber.
8. The apparatus of claim 6, further characterized by
(a) said viewing means is a transparent housing defining said chamber.

* * * * *